| United States Patent [19] | [11] Patent Number: 4,675,390 |
| Bonjouklian et al. | [45] Date of Patent: Jun. 23, 1987 |

[54] 2-DEOXYPENTOSE DERIVATIVES

[75] Inventors: Rosanne Bonjouklian; Michael L. Phillips, both of Indianapolis, Ind.

[73] Assignee: Eli Lilly and Company, Indianapolis, Ind.

[21] Appl. No.: 677,650

[22] Filed: Dec. 3, 1984

[51] Int. Cl.[4] ...................... C07H 9/140; C07H 15/02
[52] U.S. Cl. .................................... 536/4.1; 536/117; 549/222
[58] Field of Search ................. 536/117, 4.1; 549/222

[56] References Cited

U.S. PATENT DOCUMENTS 4,481,196  11/1984  Teraji et al. .................. 536/117

FOREIGN PATENT DOCUMENTS 103877  3/1984  European Pat. Off. .

Primary Examiner—Nicky Chan
Attorney, Agent, or Firm—Robert A. Conrad; Leroy Whitaker

[57] ABSTRACT

PAF analogues derived from 2-deoxyribose or 2-deoxyxylose, having cytotoxic, hypotensive and PAF agonist/antogonist properties.

16 Claims, No Drawings

2-DEOXYPENTOSE DERIVATIVES

BACKGROUND OF THE INVENTION

The term "phospholipid" is generic to several different types of compounds originating in the mammalian cell and containing long chain fatty acid esters of glycerol attached to various polar groupings. Lecithin, a phosphatidic acid ester of choline, is one of a group of such phospholipids, having structure I below

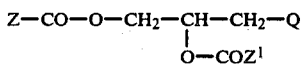

wherein Z and $Z^1$ are long straight chain alkyl or alkenyl radicals and Q is

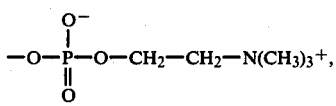

a phosphocholyl radical. A related substance is platelet-activating factor (PAF)—see Demopoulos et al, *J. Biol. Chem.*, 254, 9355 (1979)—having structure Ia below

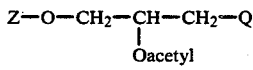

in which there is an ether linkage on C-1, a short chain fatty acid ester (acetate) at C-2, Z is $C_{16}$–$C_{18}$ alkyl and Q has its previous meaning. A number of analogues of PAF have been synthesized. Among these are compounds of structure Ib below described in *FEBS Letters*, 14 29 (1982)—see also Modell et al, *Can. Res.*, 39, 4681 (1979) which describes the activity of such compounds in selectively destroying Meth A sarcoma cells—

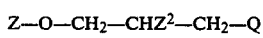

where $Z^2$ is alkyl or H; and Z and Q have their previous meanings.

A recent EPO patent 103,877 (3-28-84), Derwent No. 83598, discloses 5-phosphocholyl derivatives of methyl D-xylofuranoside in which there is a long chain alkyl (octadecyl) ether on the C-2 or C-3 hydroxy. The compounds have antitumor activity. Derivatives of deoxy pentoses are not contemplated therein.

DESCRIPTION OF THE INVENTION

This invention provides compounds of the formula

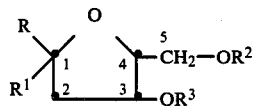

wherein, when taken singly, one of R and $R^1$ is $C_{1-3}$ alkoxy, H, OH or $C_{1-2}$ alkyl-CO-O and the other is H; and when taken together with the carbon to which they are attached, form a carbonyl; one of $R^2$ and $R^3$ is a straight chain $C_{10-18}$ aliphatic group and the other is

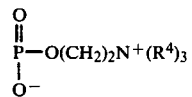

wherein each $R^4$ is individually methyl or ethyl.

The compounds according to formula I above, when one of R and $R^1$ is OH, are derived from the 5-carbon 2-deoxy sugars, 2-deoxyribose or 2-deoxyxylose. The D form of each of these sugars are given below in conventional 2-dimensional form (IIa and IIb) and in 3-dimensional representation (IIc and IId)

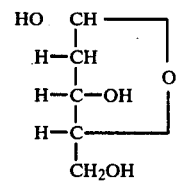

IIa
2-deoxy-D-ribose

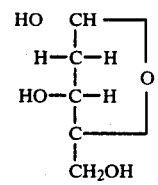

IIb
2-deoxy-D-xylose

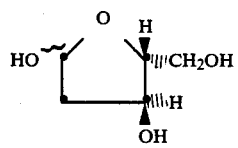

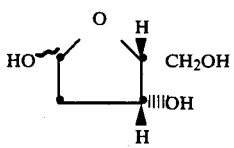

IIc
2-deoxy-D-ribose

IId
2-deoxy-D-xylose

It should be noted that in ribose, the 3-hydroxy and 4-hydroxymethyl groups are in a trans configuration, whereas in xylose, these groups are cis. In general, we prefer the trans compounds, those derived from ribose. In addition, we prefer those derivatives according to formula I wherein $R^2$ and $R^3$ represent $C_{10-18}$ straight chain aliphatic, in which the aliphatic group is saturated; ie, $C_{10-18}$ straight chain alkyl, and particularly those derivatives in which one of $R^2$ and $R^3$ is n-$C_{14-18}$ alkyl. We also prefer derivatives of choline for $R^2$ or $R^3$; ie, all $R^4$'s are methyl. We also prefer those derivatives in which one of R and $R^1$ is $C_{1-2}$ alkoxy.

When one of R and $R^1$ is $C_{1-3}$ alkoxy, the alkoxy group can be either α or β using 2-deoxy-D-ribose for illustrative purposes only. The 1-methyl ethers, for example (R is $CH_3O$), can be represented as follows

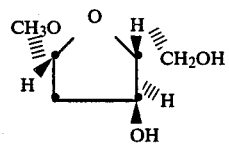

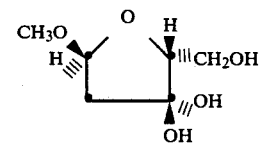

IIIa

IIIb

IIIa is named systematically as β-methyl 2-deoxy-D-ribofuranoside and IIIb as α-methyl 2-deoxy-D-ribofuranoside. The corresponding compounds from 2-deoxy-D-xylose are named β-methyl 2-deoxy-D-xylofuranoside and α-methyl 2-deoxy-D-xylofuranoside.

While all of the above illustrations have been to D-sugars, the L isomers (mirror images) also are included within the scope of formula I. 2-deoxy-L-ribose and 2-deoxy-L-xylose are given below (IIIc and IIId)

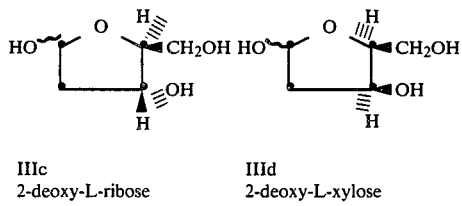

IIIc
2-deoxy-L-ribose

IIId
2-deoxy-L-xylose

Derivatives of both the α and β methyl furanosides of IIIc and IIId are also contemplated by this invention, and fall within its scope.

Finally, when both R and $R^1$ in formula I form a carbonyl with the carbon to which they are attached, a substituted δ-butyrolactone is described as in IVa, and when both R and $R^1$ and H, a tetrahydrofuran IVb is described, using products derived from 2-deoxy-D-ribose for illustrative purposes only.

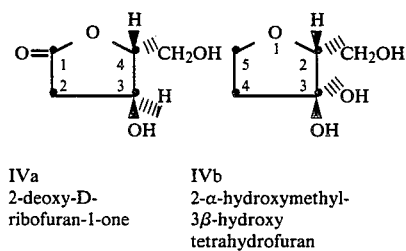

IVa
2-deoxy-D-ribofuran-1-one

IVb
2-α-hydroxymethyl-3β-hydroxy tetrahydrofuran

Derivatives of the compounds isomeric with IVa, 2-deoxy-D-xylofuran-1-one, 2-deoxy-L-ribofuran-1-one and 2-deoxy-L-xylofuran-1-one are also included within the scope of I above. Likewise, IVb depicts only one of the four stereoisomers represented by the formula IVc

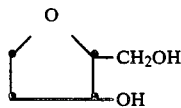

IVc and derivatives of all four stereoisomers are included within the scope of I above.

In formula I above, if, for example, $R^2$ is phosphocholyl ($R^4$ is methyl), $R^3$ is n-hexadecyl, R is hydroxy and $R^1$ is H, the compound is named as 2-deoxy-3-n-hexadecyl-5 phosphocholyl-D-ribofuran-1-one. If $R^3$ is phosphocholyl ($R^4$ is $CH_3$), $R^2$ n-hexadecyl, R is hydroxy and $R^1$ is H, the compounds named 2-deoxy-3-phosphocholyl-5-n-hexadecyl-D-ribofuran-1-one. The orientation of the substituent on $C_1$, $C_3$ and $C_4$ is fixed since D-ribose is specified as the starting material. In particular, with D-ribose, the phosphocholine group and the long chain aliphatic ether group ($R^2CH_2$ and $R^3$) are fixed in a trans orientation, whereas in 2-deoxy-D-xylose, the orientation is cis.

Groups illustrative of R or $R^1$ in the above formulas include methoxy, ethoxy or n-propoxy. Those illustrative of $R^2$ or $R^3$ when a $C_{10-18}$ aliphatic radical is represented include the alkyl groups; decyl, undecyl, dodecyl, tridecyl, tetradecyl, pentadecyl, hexadecyl and octadecyl; the alkenyl groups, undec-trans 4-enyl, undec-trans 2-enyl, undec-11-enyl, tridec-9-enyl, tetradec-6-enyl, pentadec-trans 3-enyl, pentadec-6-enyl, pentadec-cis 9-enyl, heptadec-cis 9-enyl, heptadec-cis-6-enyl, heptadec-11-enyl, heptadec-cis 12-enyl, and heptadec-cis 12-enyl; the alkynyl group, heptadec-6-ynyl(Tariryl) and heptadec-9-ynyl; and the polyunsaturated groups, pentadec-2,4,8,10-tetraenyl, heptadec-cis 5,11-dienyl, heptadec-9,12-dienyl, heptadec-trans 10,trans 12-dienyl, heptadec-cis 7,cis 11-dienyl, heptadec-trans 11-ene-9-ynyl, heptadec-cis 9,cis 12,cis 15-trienyl, heptadec-6,9,12-trienyl, heptadec-9,11,13-trienyl, heptadec-trans 13-ene-9,11-diynyl, heptadec-trans 11,trans 13-dien-9-ynyl, heptadec-8,10,12-trienyl, heptadec-5,11,14-trienyl, heptadectrans 5,cis 9,cis 12-trienyl, heptadec-17-ene-9,11-diynyl, heptadec-9,11,13,15-tetraenyl, heptadec-cis 6,-cis 9,cis 12,cis 15-tetraenyl, and the like groups.

Compounds of this invention derived from 2-deoxy-D-ribose, where $R^2$ is a phosphocholine-type group and $R^3$ is, for illustrative purposes only, n-hexadecyl, are named as follows:

α-methyl 2-deoxy-3-n-hexadecyloxy-5-phosphocholyl-D-ribofuranoside (R is α-methoxy, $R^1$ is H, $R^4$ is methyl); β-methyl 2deoxy-3-n-hexadecyl-5-phosphocholyl-D-ribofuranoside ($R^1$ is β-methoxy, R is H, $R^4$ is methyl); α-methyl 2-deoxy-3-phosphocholyl-5-n-hexadecyl-D-ribofuranoside, (R is α methoxy, $R^1$ is H, $R^4$ is methyl); 2-deoxy-3-n-hexadecyl-5-phosphocholyl-D-ribofuran-1-one (R and $R^1$ are=0, $R^4$ is methyl). Compounds derived from 2deoxy-D-ribose where $R^3$ is n-tetradecyl for illustrative purposes and $R^2$ is phosphocholyl are named as follows: α-methyl 2-deoxy-3-phosphocholyl-5-n-tetradecyl-D-ribofuranoside (R is α-methoxy, $R^1$ is H, $R^4$ is methyl); 2-deoxy-3-phosphocholyl-5-n-tetradecyl-D-ribofuran-1-one (R+$R^1$ are=0, $R^4$ is methyl).

Illustrative compounds based on 2-deoxy-L-ribose, 2-deoxy-L-xylose or 2-deoxy-D-xylose, include α-n-propyloxy 2-deoxy-3-n-decyl-5-phosphocholyl-L-ribofuranoside (R is α-n-propyloxy, $R^1$ is H, $R^3$ is n-decyl, $R^4$ is $CH_3$); β-n-propyloxy 2-deoxy-3-phosphocholyl-5-n-dec-3-enyl-L-xylofuranoside ($R^1$ is β-n-propyloxy, R is H, $R^2$ is n-dec-3-enyl and $R^4$ is $CH_3$); 2-deoxy-3-phosphocholyl-5-n-octadec-3,5-dienyl-D-xylofuran-1-one (R+$R^1$ are=0, $R^3$ is n-octadec-3,5-dienyl, $R^4$ is $CH_3$); β-methyl 3-phosphocholyl-5-n-hexadec-3-ynyl-L-xylofuranoside (R=H, $R^1$=β-methoxy, $R^3$ is n-hexadec-3-ynyl and $R^4$ is $CH_3$).

Tetrahydrofurans coming within the scope of this invention include:

2β-n-tridecyloxymethyl-3α-phosphocholyloxy tetrahydrofuran (R+$R^1$=H, $R^2$ is n-tridecyl, $R^4$ is $CH_3$); 2α-phosphocholyloxymethyl-3-α-n-tetradecyloxytetrahydrofuran (R and $R^1$=H, $R^4$ is $CH_3$, $R^3$ is n-tetradecyl.)

Compounds of this invention, according to I above when one of R and $R^1$ is $C_{1-3}$ alkoxy and the other is H, are prepared from, for example, α[or β]-$C_{1-3}$ alkyl 2-deoxy-D(or L)-ribofuranoside or α(or β)-$C_{1-3}$ alkyl 2-deoxy-D(or L)-xylofuranoside. These furanosides are in turn, either commercially available or are readily prepared by standard procedures. By convention, β-methyl 2-deoxy-D-ribofuranoside, can be for example, represented by either Va (2-dimensional) or Vb (3-dimensional structures

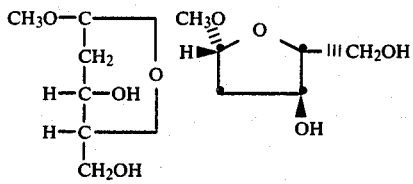

Va    Vb

The corresponding α-methyl 2-deoxy-D-ribofuranoside is similarly conventionally represented by Vc and Vd.

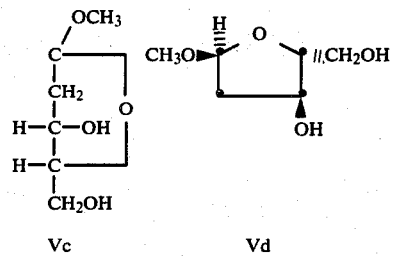

Vc    Vd

In the 2-dimensional structure, α and β refer to the presence of the methoxy on the opposite side of the plane of the furan ring (α) or on the same side (β). Thus, α-methyl 2-deoxy-L-ribofuranoside would be represented by Ve and the 3-dimensional formula Vf.

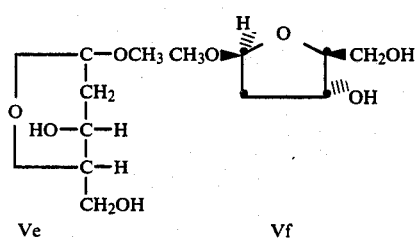

Ve    Vf

The correesponding xylose starting materials can be represented 2-dimensionally by VIa-d.

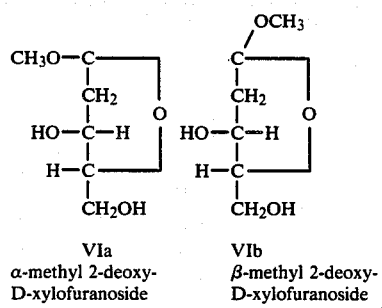

VIa    VIb
α-methyl 2-deoxy-    β-methyl 2-deoxy-
D-xylofuranoside    D-xylofuranoside -continued

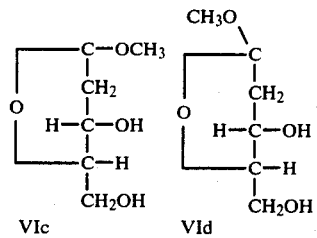

VIc    VId
α-methyl 2-deoxy-    β-methyl 2-deoxy-
L-xylofuranoside    L-xylofuranoside The 3-dimensional configurations of the starting materials can be easily constructed by those skilled in the art from the above disclosure.

In order to prepare the compounds of this invention, starting with an α(or β)-$C_{1-3}$ alkyl D-(or L)-ribo(or xylo)furanoside, the primary alcohol at C-5 is protected with an acid-unstable ether group such as a trityl (triphenylmethyl) ether protecting group. The 3-hydroxyl is reacted with a $C_{10-18}$ straight-chain aliphatic halide or other alkylating derivative, under basic (Williamson) conditions to form a 3-$C_{10-18}$ straight-chain aliphatic ether. The trityl group at C-5 is then removed and a phosphocholine-type $$(O-\overset{\overset{O}{\|}}{\underset{O^-}{P}}-O(CH_2)_2N^+(R^4)_3)$$

moiety built up at C-5 by successive reaction with $POCL_3$ and choline tosylate (or other replaceable ester group) to yield the desired product. Alternatively, with the trityl ether group protecting the C-5 hydroxy, the C-3 hydroxyl can be protected with an acid stable protecting group such as a benzyl ether. The diprotected compound is then selectively deprotected by treatment with acid at C-5, and the now-free C-5 hydroxyl is reacted with a $C_{10-18}$ straight-chain aliphatic halide to form the desired long-chain aliphatic ether at C-5. The C-3 protecting group is then removed. If a benzyl ether protecting group has been used, the ether can be split by hydrogenolysis using a noble metal supported catalyst. The now-free C-3 hydroxyl is available for reaction with $POCl_3$ and that product reacted with choline tosylate or other suitable choline derivative, to yield a 3-phosphocholine derivative with an aliphatic ether at C-5.

These reactions are illustrated in Reaction Scheme 1 below, using n-hexadecyl as an example of a $C_{10-18}$ straight-chain aliphatic group and choline itself to form the phosphocholine.

Reaction Scheme 1

-continued
Reaction Scheme 1
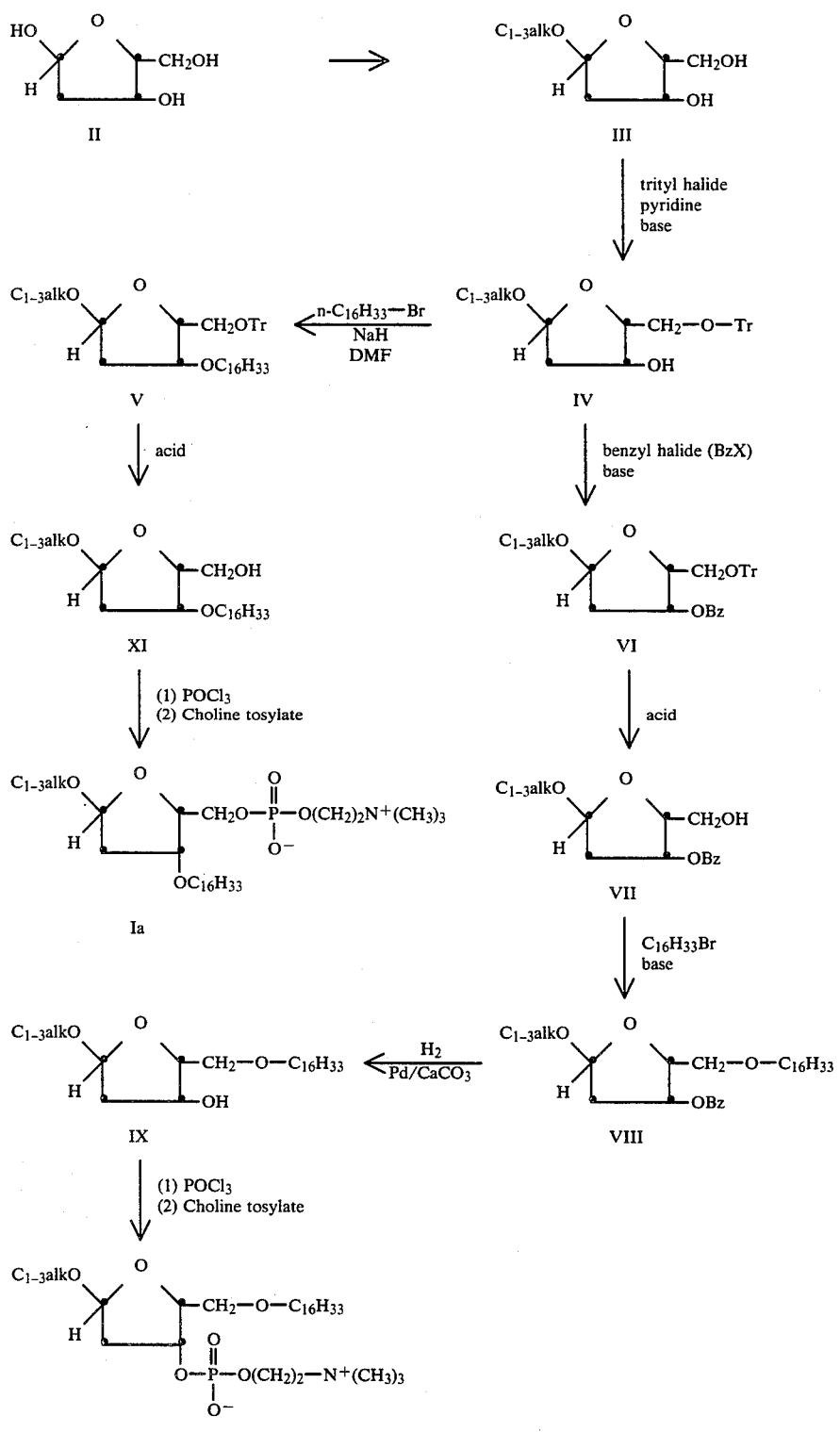
Ia is I wherein $R^2$ is n-$C_{16}H_{33}$, and $R^3$ is 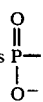, Ib is I wherein $R^2$ is

Reaction Scheme 1
-continued

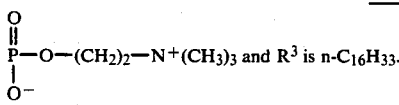
and $R^3$ is n-$C_{16}H_{33}$.

In the above reaction scheme, the 2-deoxy 5-carbon sugar (II) is alkylated to yield an α or β-alkyl furanoside (III) by standard procedures. The primary alcohol group at C-5 is then protected by a trityl ether group or by other similar acid-unstable protecting group, using a trityl halide in the presence of base (pyridine, 4-dimethylaminopyridine and the like) in a mutual inert solvent—DMF, DMA and the like—to yield IV. Other protective groups which will react selectively with a primary hydroxyl in the presence of a secondary hydroxyl are set forth in *Protective Groups in Organic Synthesis*, Greene (John Wiley & Sons, New York, 1981). These protective groups selective for primary alcohols include the t-butyl ether, the α-naphthyldiphenylmethyl ether, the p-methoxyphenyldiphenylmethylether, the p-(p'-bromophenacyloxy)phenyldiphenyl ether and the like. Next, to prepare the 3-phosphocholine (Ib) ether the secondary alcohol is protected with a protecting group not subject to acid hydrolysis, particularly a benzyl or substituted benzyl ether, to yield a diprotected (on the C-3 and C-5 hydroxyls) 2-deoxyfuranoside (VI). Next, the trityl group is removed by acid, p-toluene sulfonic, trifluoroacetic, Bio-Rad resin, BF$_3$-etherate or the like in an organic solvent (THF, CH$_2$Cl$_2$/MeOH, DMF) to yield the free primary hydroxyl (VII). Reaction of this primary hydroxyl with a straight-chain aliphatic halide, illustratively n-hexadecyl bromide, yields a diether acetal (VIII). Standard Williamson conditions—base (NaH) in a mutual inert solvent—are employed. The protecting group at C-3, illustratively a benzyl group, is now removed, conveniently by hydrogenolysis at low hydrogen pressure over a noble metal catalyst, to yield IX. The now-free secondary hydroxyl is reacted successively with POCl$_3$ and choline tosylate to yield an inner salt of this invention (I wherein one of R is R$^1$ is methyl and the other is H, R$^2$ is n-hexadecyl, R$^3$ is a phosphocholine

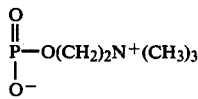

group in which R$^4$ is methyl).

Alternatively, to prepare compounds of formula Ia or the like, the tritylated intermediate (IV) is reacted with a straight chain C$_{10-18}$ aliphatic halide, illustratively n-hexadecylbromide, to yield a 3-C$_{10-18}$ straight chain aliphatic ether (V). The trityl group at C-5 is removed with acid as before to yield a compound with a free hydroxyl, which compound can be reacted successively with POCl$_3$ and choline tosylate to yield the isomeric 5-phosphocholine—a C$_{1-3}$ alkyl 2-deoxy-3-straight chain aliphatic-5-phosphocholine derivative (Ia) where one of R and R$^1$ is C$_{1-3}$ alkyl and the other is H, R$^3$ is n-hexadecyl and R$^2$ is a phosphocholine-type group wherein R$^4$ is methyl.

Next, to prepare a compound according to I wherein one of R and R$^1$ is OH, R$^2$, R$^3$ and R$^4$ remaining the same, a product according to Ia or Ib is hydrolysed to the free sugar (an aldehyde group at C-1) with strong acid. Oxidation of this aldehyde to the acid, a butyrolactone, is readily accomplished with aqueous Br$_2$—see *J.A.C.S.*, 51, 2225 (1929) for example for reaction conditions. On the other hand, reduction of the acetal (Ia or Ib) with triethylsilane in the presence of a Lewis acid cleanly yields the tetrahydrofuran (a compound according to I wherein R and R$^1$ are both H).

It should be noted that compounds according to I derived from D-ribose possess the same transchiralty as PAF.

This invention is further illustrated by the following specific example.

EXAMPLE 1

Preparation of Methyl 2-Deoxy-5-trityl-D-ribofuranoside

About 25 g of 2-deoxy-D-ribose were placed in a dried 2000 ml round-bottomed flask under a stream of N$_2$. The flask was cooled, and 873 ml of 0.05% methanolic hydrogen chloride added with stirring. After 15 minutes, during which time the sugar had dissolved, about 5 g of silver carbonate were added, and the resulting reaction mixture stirred vigorously for 0.5 hours. The reaction mixture was filtered thru hyflosupercel ® and the filter cake washed thoroughly with methanol. Evaporation of the methanol from the filtrate left, as a residue, about 27.5 g (100% yield) of a mixture of α and β-methyl 2-deoxy-D-ribofuranoside. This compound was dissolved in 558 ml of pyridine. 76.93 g of tritylchloride were added under N$_2$, and the reaction mixture was stirred at room temperature for about 72 hours at which time TLC (SiO$_2$; 3:1 cyclohexane/ethyl acetate) showed that the reaction had gone to completion. The pyridine was removed by evaporation under reduced pressure, and the residue, comprising methy 2-deoxy-5-trityl-D-ribofuranoside formed in the above reaction, was dissolved in a mixture of chloroform and water. The chloroform layer was separated, and the aqueous layer extracted with chloroform. The chloroform extracts were combined; the combined extracts were washed with brine and then dried. Evaporation of the solvent yielded a residue which was purified by preparative HPLC. 65.4 g (90% yield) of methyl 2-deoxy-5-trityl-D-ribofuranoside were thus obtained.

Following the above procedure, α-methyl 2-deoxy-D-xylofuranoside was tritylated on the primary hydroxyl to yield α-methyl 2-deoxy-5-trityl-D-xylofuranoside having the following properties:
Rf=0.25 (3:1 cyclohexane/ethylacetate-solvent A; SiO2); mass spectrum (relative intensity) 390 (M+, 100); rotation of plane polarized light [α]$_D^{25}$+27.4 (C=1, MeOH); NMR δ 5.15 (app t, 1, H-1), 4.55 (m, 1, H-3), 4.17 (m, 1, H-4), 3.37 (s, 3, —OCH$_3$).

EXAMPLE 2

Preparation of Methyl 2-Deoxy 3-n-hexadecyl-5-trityl-D-ribofuranoside

An NaH dispersion in oil (60%) containing 11.12 g of NaH was placed in a 2000 ml 3-neck round-bottomed flask under N$_2$. The oil was removed by washing with hexane according to standard procedures. A solution of 59.7 g of methyl 2-deoxy-5-trityl-D-ribofuranoside from Example 1 in 306 ml of DMF was added to the solid NaH residue, still under $N_2$. After about 30 minutes, 70.1 ml. of n-hexadecylbromide were added. The reaction mixture was heated at about 50° C. for about 24 hours during which time three additional 11.12 g portions of oil-free NaH and one 24 ml portion of n-hexadecyl bromide were added. The progress of the reaction was followed by TLC. When TLC indicated that the reaction had gone substantially to completion, excess NaH was destroyed by the cautious addition of water. The volatile constituents were removed by evaporation. Chloroform and water were added to the residue. The chloroform layer was separated, and the aqueous layer extracted with chloroform. The chloroform extracts were combined, washed with brine and then dried. Evaporation of the solvent from the combined extracts yielded 134.2 g of an estimated 3:2 mixture (by TLC) of 3-n-hexadecyl ether and starting material. Preparative HPLC was used to separate the two materials. 47.6 g (50.6% yield) of methyl 2-deoxy-3-n-hexadecyl-5-trityl-D-ribofuranoside were obtained, and 23.2 g of starting material was recovered.

EXAMPLE 3

Preparation of Methyl 2-Deoxy-3-n-hexadecyl-D-ribofuranoside

A solution of 1.365 g of methyl 2-deoxy-3-n-hexadecyl-5-trityl-D-ribofuranoside in 11.1 ml of methylene dichloride were placed in a 50 ml round-bottomed flask. 11.1 ml of MeOH were added with stirring at room temperature followed by 42.7 mg of p-toluene sulfonic acid monohydrate. After 4 hours, TLC ($SiO_2$; 3:1 cyclohexane/ether or 5:1 cyclohexane/ethyl acetate) indicated reaction was substantially complete. The reaction mixture was then diluted with methylene dichloride, and the organic solution extracted with an equal volume of 0.1N aqueous sodium hydroxide (pH=12.1). The sodium hydroxide extract was washed with methylene dichloride. The methylene dichloride extracts were combined, washed with brine and dried. Evaporation of the solvent yields a solid residue which was purified by chromatography over $SiO_2$. The solid residue was loaded onto the $SiO_2$ column as a chloroform solution, and the column was eluted with a cyclohexane containing increasing amounts of ethyl acetate (0–20%). Two major fractions were obtained. The faster moving (first to be eluted) fraction was β-methyl 2-deoxy-3-n-hexadecyl-D-ribofuranoside (349.6 mg) and the slower moving (last to be eluted) fraction was α-methyl 2-deoxy-3-n-hexadecyl-D-ribofuranoside.

EXAMPLE 4

Preparation of Methyl 2-Deoxy-3-benzyl-D-ribofuranoside

A solution of 10.2 g of methyl 2-deoxy-5-trityl-D-ribofuranoside was added under $N_2$ to 2.090 g of NaH solid isolated from a 60% oil dispersion by the procedure outlined in Example 2. After stirring the mixture under $N_2$ for about 30 minutes, 3.91 ml of benzyl chloride were added, and the reaction mixture heated to about 65° C. overnight. Two additional grams of NaH and 3.91 ml additional benzyl chloride were added. When TLC ($SiO_2$; 3:1 cyclohexane/ethyl acetate) indicated that the reaction had gone substantially to completion, water was added dropwise to decompose excess NaH. The reaction mixture was worked up and the product isolated as in Example 2; crude yield of methyl 2-deoxy-3-benzyl-5-trityl-D-ribofuranoside=15.1 g.

The above compound was detritylated with p-toluene sulfonic acid by the procedure of Example 3, and the mixture of α and β-methyl 2-deoxy-3-benzyl-D-ribofuranosides thus obtained separated by HPLC over $SiO_2$. The faster moving component was the β-methyl D-ribofuranoside derivative; yield=1.7722 g. The slower moving component was the α-methyl isomer; yield=1.8979 g.

Following the above procedure, α-methyl 2-deoxy-5-trityl D-xylofuranoside was reacted with benzyl chloride via the sodium salt (NaH in DMF) to yield α-methyl-2-deoxy-3-benzyl-5-trityl-D-xylofuranoside having the following physical properties:

$R_f$=0.61 (same system as Example 1); mass spectrum (relative intensity) 243 (100), 237 (M-trityl, 30); NMR ($CDCl_3$) δ 5.14 (d of d, 1, H-1), 4.1–4.4 (2 m, 4H, H-3, H-4, $CH_2C_6H_5$), 3.4 (s, 3H, $OCH_3$). Still following the above procedure, α-methyl 2-deoxy-3-benzyl-5-trityl-D-xylofuranoside was detritylated with p-toluene sulfonic acid in methylene dichloride/methanol to yield α-methyl 2-deoxy-3-benzyl-D-xylofuranoside having the following physical properties.

Mass spectrum (relative intensity) 237 (M-1, 38), 207 (M-$OCH_3$, 23); NMR ($CDCl_3$) δ 5.1 (app t, 1, H-1), 3.7–4.45 (3m, 6), 3.3 (s, 3, $OCH_3$), 2.1 (d of d, 2, H-5).

EXAMPLE 5

Preparation of α-Methyl 2-Deoxy-5-n-hexadecyl-D-ribofuranoside

Following the procedure of Example 2, 276.2 mg of α-methyl 2-deoxy-3-benzyl-D-ribofuranoside in 23 ml of DMF were added to 69.5 mg of NaH. After the NaH had reacted to form the $Na^+$ salt at the C-5 hydroxyl, 0.53 ml of n-hexadecylbromide were added. The reaction was worked up and the product isolated by the procedure of Example 2. The crude product was chromatographed over silica using cyclohexane containing increasing amounts of ether (0–10%) as the eluant. 233.6 mg (50.5% yield) of purified α-methyl 2-deoxy-3-benzyl-5-n-hexadecyl-D-ribofuranoside were obtained.

The above procedure was repeated with β-methyl 2-deoxy-3-benzyl-D-ribofuranoside to yield (54.3%) β-methyl-3-benzyl-5-n-hexadecyl-D-ribofuranoside, and with α-methyl 2-deoxy-3-benzyl-D-xylofuranoside to yield α-methyl 2-deoxy-3-benzyl-5-n-hexadecyl-D-xylofuranoside having the following physical properties:

$R_f$0.65 ($SiO_2$, solvent A) mass spectrum (relative intensity); 462 ($M^+$, 100), 430 (M-$CH_3OH$, 30), NMR ($CDCl_3$) δ 5.09 (d of d, 1, H-1), 4.44 (s, 2), 4.18 (m, 2, H-3, H-4), 3.36 (s, 3, $OCH_3$).

A solution of 1.0555 g of α-methyl 2-deoxy-3-benzyl-5-n-hexadecyl-D-ribofuranoside in 50 ml of ethanol was hydrogenated at 40 psi over 0.25 g of 5% Pd/$CaCO_3$ in an Adams machine. After 1.5 hours, the theoretical amount of $H_2$ having been absorbed and TLC indicating absence of starting material, the hydrogenation solution was filtered, and the ethanol evaporated from the filtrate to yield 824 mg (100% yield) of α-methyl 2-deoxy-5-n-hexadecyl-D-ribofuranoside.

The above hydrogenolysis was repeated with the β-methyl furanoside to yield quantitatively β-methyl 2-deoxy-5-n-hexadecyl-D-ribofuranoside.

The above hydrogenolysis was repeated with α-methyl 2-deoxy-3-benzyl-5-n-hexadecyl-D-xylofuranoside to produce α-methyl 2-deoxy-5-n-hexadecyl-D-xylofuranoside having the following physical properties:

$R_f$ 0.33 (SiO$_2$, solvent A); NMR (CDCl$_3$) δ 5.2 (app t, 1, H-1), 4.57 (M, 1, H-4), 4.1 (m, 1, H-3), 3.8 (d, 2, H-5), 3.4 (s, 3, OCH$_3$), 216 (app t, 2, H-2).

EXAMPLE 6

Preparation of β-Methyl 2-Deoxy-3-phosphocholyl-5-n-hexadecyl-D-ribofuranoside

To a solution of POCl$_3$ (0.14 ml) in dry THF (1 ml) was added dropwise a solution of β-methyl 2-deoxy-5-n-hexadecyl-D-ribofuranoside (0.372 mg) and Et$_3$N (0.28 ml) in 5 ml of THF. After 45 min, the resulting suspension was quickly filtered, evaporated and redissolved in a solution of pyridine (0.62 ml) in 6 ml of CHCl$_3$. Choline tosylate (0.606 g) was then added, and after 5 hours, 0.2 ml H$_2$O were introduced. After 30 minutes, the reaction mixture was diluted with CHCl$_3$, H$_2$O and MeOH (9:3:4). The organic layer was washed with 5% aq. NaHCO$_3$, dried, concentrated and the residue chromatographed over silica (eluant was CHCl$_3$→1:2 CHCl$_3$/MeOH) to yield β-methyl 2-deoxy-3-phosphocholyl-5-n-hexadecyl-D-ribofuranoside (0.357 mg, 66.5%);

Physical characteristics: $R_f$ 0.25 (SiO$_2$; 10:5:1 CHCl$_3$/MeOH/NH$_3$-Solvent B); $[\alpha]_D^{25}$ −12.0° (c 1.0, CHCl$_3$); NMR (CDCl$_3$) δ 2.28 (m, 2, H-2), 3.34 (s, 3, OCH$_3$), 3.39 (s, 9, N$^+$(CH$_3$)$_3$), 4.20 (m, 1, H-4), 4.73 (m, 1, H-3), 5.10 (dd, 1, J=3.05 Hz and 4.88 Hz, H-1); MS, m/e (relative intensity) 538 (m$^+$+1, 1), 184 (32), 73(100).

Mol. wt., Calc'd. for C$_{27}$H$_{57}$NO$_7$P: 538.3873. Found: 538.3877.

Anal.: Calc'd. for C$_{27}$H$_{56}$NO$_7$P.2H$_2$O: C, 56.52; H, 10.54; N, 2.44. Found: C, 59.98; H, 10.49; N, 2.85.

Other compounds preparable by the above procedure include α-methyl 2-deoxy-3-phosphocholyl-5-hexadecyl-D-ribofuranoside having the following physical characteristics:

$R_f$ 0.25 (SiO$_2$, Solvent B); $[\alpha]_D^{25}$ +52.6° (C 1.0, CHCl$_3$); NMR (CDCl$_3$) δ 2.07 and 2.34 (d of m, 2, H-2), 4.27 (m, 1, H-4), 4.65 (m, 1, H-3), 5.05 (dd, 1, J=1 and 6.1 Hz, H-1); MS, m/e (relative intensity) 538 (m$^+$+1, 0.3), 184 (100). Mol. wt. calc'd. for C$_{27}$H$_{57}$NO$_7$P: 538.3873, Found: 538.3866.

Methyl 2-deoxy-3-n-hexadecyl-5-phosphocholyl-D-ribofuranoside $R_f$ 0.19 (SiO$_2$, Solvent B); $[\alpha]_D^{25}$ +59.4° (C 1.0, MeOH); NMR (CDCl$_3$) δ 1.95 and 2.22 (d of m, 2, H-2), 3.36 (s, 3, OCH$_3$), 3.4 (s, 9, N$^+$(CH$_3$)$_3$), 3.8–4.2 (m, 6H), 5.0 (d, 1, J=2 Hz, H-1); MS, m/e (relative intensity) 538 (M$^+$+1, 40), 264 (70), 184 (100)

Anal.: Calc'd. for C$_{27}$H$_{56}$NO$_7$P.H$_2$O=C, 58.35; H, 10.52; N, 2.52. Found: C, 58.15; H, 10.21; N, 2.31.

β-Methyl 2-deoxy-3-n-hexadecyl-5-phosphocholyl-D-ribofuranoside $R_f$ 0.19 (B); $[\alpha]_D^{25}$ −23.2° (C 1.0, MeOH); NMR (CDCl$_3$) δ 2.1 (m, 2, H-2), 3.33 (s, 3, OCH$_3$), 3.4 (s, 9, N$^+$(CH$_3$)$_3$), 3.8–4.2 (m, 6H), 5.1 (d of d, 1, J=1 Hz, H-1); MS, m/e (relative intensity) 264 (m-OCH$_3$—OC$_{16}$H$_{33}$, 86), 184 (100). An analytical sample was prepared by recrystallization from CH$_2$Cl$_2$/acetone.

Anal.: Calc'd. for C$_{27}$H$_{56}$NO$_7$P: C, 60.31; H, 10.50; N, 2.60. Found: C, 60.58; H, 10.49; N, 2.49.

α-Methyl 2-deoxy-3-phosphocholyl-5-n-hexadecyl-D-xylofuranoside $R_f$ 0.29 (SiO$_2$, Solvent B); NMR (CDCl$_3$) δ 5.1 (m, 1, H-1), 4.8 (m, 1, H-3), 4.2 (m, 2), 3.6–4.0 (brd m, 5H) 3.4 (brd s, 13); MS, (relative intensity) 538 (M+1)

EXAMPLE 7

Preparation of 2-Deoxy-3-phosphocholyl-n-5-hexadecyl-D-ribose

A solution of β-methyl 2-deoxy-3-phosphocholyl-5-n-hexadecyl-D-ribofuranoside (0.257 g) in 0.55N HCl (5.2 ml) was heated to 70° with stirring for 1.5 hours. After cooling, the solution was neutralized and lyophilized. The residue was then extracted with CHCl$_3$, the chloroform solution filtered and concentrated, and the concentrate chromatographed (CHCl$_3$→1:1 CHCl$_3$/MeOH) to give 2-deoxy-3-phosphocholyl-5-n-hexadecyl-D-ribose (0.247 g, 99%) with these physical characteristics: $R_f$ 0.12 (SiO$_2$, Solvent B); $[\alpha]_D^{25}$ +17.0° (C 1.0, MeOH); NMR (CDCl$_3$) δ 2.2 (m, 2, H-2), 3.35 (s, 9, N$^+$(CH$_3$)$_3$), 5.55 (m, 1, H-1); MS, m/e (relative intensity) 524 (m$^+$+1, 1), 184 (100). Analysis: Calc'd. for C$_{26}$H$_{55}$NO$_7$P: Mol wt, 524.3716. Found: 524.3688.

Also prepared by the above procedure from α-methyl-3-n-hexadecyl-5-phosphocholyl-D-ribofuranoside was 2-Deoxy-3-n-hexadecyl-5-phosphocholyl-D-ribose leaving the following characteristics: $R_f$ 0.14 (SiO$_2$, Solvent B); $[\alpha]_D^{25}$ +13.2° (C 1.0, MeOH); NMR (CDCl$_3$) δ 2.1 (m, 2, H-2), 5.48 and 5.57 (2m, 1, H-1 isomers in 3:7 ratio); MS, m/e (relative intensity) 524 (m$^+$+1, 15), 264 (100), 184 (100). Anal.: Mol. wt, Calc'd. for C$_{26}$H$_{55}$NO$_7$P: 524.3716. Found: 524.3748.

EXAMPLE 8

Preparation of 2-Deoxy-3-phosphocholyl-5-n-hexadecyl-D-ribofuran-1-one

Barium carbonate (0.333 g) was added to a solution of 2-deoxy-3-phosphocholyl-5-n-hexadecyl-D-ribose (0.631 g) in 1.8 ml H$_2$O. The resulting solution was cooled to 0°, and 7.4 μl of Br$_2$ were added. After 5.5 hours, the material was lyophilized. The lyophilate was extracted into CHCl$_3$, the CHCl$_3$ solution concentrated, and the concentrate chromatographed (CHCl$_3$→1:1 CHCl$_3$/MeOH) to afford 2-deoxy-3-phosphocholyl-5-n-hexadecyl-D-ribofuran-1-one (0.028 g, 45%); having these physical characteristics: $R_f$ 0.25 (SiO$_2$, Solvent B); IR (film) 1770 cm$^{-1}$; NMR (CDCl$_3$) δ, 2.2–3.0 (2, m, H-2), 3.35 (9, s, N$^+$(CH$_3$)$_3$), 3.4–5.0 (m, 10); MS m/e (relative intensity) 522 (m$^+$+1, 1), 184 (100).

Also prepared by the above procedure was 2-deoxy-3-n-hexadecyl-5-phosphocholyl-D-ribofuran-1-one having these physical characteristics:

$R_f$ 0.2 (SiO$_2$, Solvent B); $[\alpha]_D^{25}$ +7.3° (C 1.0, CHCl$_3$); IR (film) 1770 cm$^{-1}$; NMR (CDCl$_3$) δ 2.5 and 3.0 (ddd, 2, H-2), 3.38 (s, 9, N$^+$(CH$_3$)$_3$); MS, m/e (relative intensity) 522 (m$^+$+1, 100), 184 (100); Anal.: Mol wt, Calc'd. for C$_{26}$H$_{53}$NO$_7$P: 522.3560. Found: 522.3580.

EXAMPLE 9

Preparation of 1,2-Dideoxy-3-n-hexadecyl-D-ribofuranose

To a chilled (0°) solution of β-methyl 2-deoxy-3-n-hexadecyl-D-ribofuranoside (0.288 g) in 10 ml of $CH_3CN/CH_2Cl_2$(2:1) was added $Et_3SiH$ (0.12 ml) and an equimolar amount of boron trifluoride etherate. The resulting suspension was rapidly stirred for 20 min., and then quenched with $K_2CO_3$ (0.16 g). The reaction mixture was diluted with $CHCl_3/H_2O$. The organic phase was separated, washed with 0.1N HCl, dried, and concentrated in vacuo. The concentrate was chromatographed over $SiO_2$ (cyclohexane→10:1 $C_6H_{12}$/EtOAc) to yield 1,2-dideoxy-3-n-hexadecyl D-ribofuranose (0.187 g, 71%); having the following characteristics:

$R_f$0.13 ($SiO_2$, Solvent A); NMR ($CDCl_3$) δ 2.0 (m, 2, H-2), 3.3–4.0 (m, 9); MS, m/e (relative intensity) 343 (m$^+$+1, 100), 324 (10), 311 (35).

Also prepared by the above procedure was 1,2-dideoxy-5-n-hexadecyl-D-ribofuranose, having these physical characteristics: $R_f$0.14 ($SiO_2$, Solvent A); NMR ($CDCl_3$) δ 1.8–2.3 (m, 2, H-2), 2.6 (s, 1, OH), 3.45–4.4 (2m, 7); MS, m/e (relative intensity) 343 (m$^+$+1, 72), 87 (100).

EXAMPLE 10

Preparation of 1,2-Dideoxy-3-phosphocholyl-5-n-hexadecyl-D-ribofuranose

Following the procedure of Example 6, 1,2-dideoxy-3-phosphocholyl-5-n-hexadecyl-D-ribofuranose was synthesized from 1,2-dideoxy-5-n-hexadecyl-D-ribofuranose. The compound had the following characteristics: $R_f$0.15 ($SiO_2$, Solvent B); NMR ($CDCl_3$) δ 2.1 (m, 2, H-2), 3.36 (s, 13H), 3.7–4.6 (3m, 8H); MS, m/e (relative intensity) 508 (m$^+$+1, 12), 184 (100). Anal.: Mol wt, Calc'd. for $C_{26}H_{55}NO_6P$: 508.3767. Found: 508.3773.

1,2-Dideoxy-3-n-hexadecyl-5-phosphocholyl-D-ribofuranose was synthesized from 1,2-dideoxy-3-n-hexadecyl-D-ribofuranose by the same procedure. The compound had these physical characteristics:

$R_f$0.16 ($SiO_2$, Solvent B); NMR ($CDCl_3$) δ 1.95 (m, 2, H-2), 3.36 (s, 11H), 3.6–4.4 (m, 10H); MS, m/e (relative intensity) 508 (m$^+$+1, 100), 184 (95). Anal.: Calc'd. for $C_{26}H_{54}NO_6P \cdot \frac{1}{2}H_2O$: C, 60.44; H, 10.73; N, 2.71. Found: C, 60.28; H, 10.88; N, 2.55.

EXAMPLE 11

Preparation of 1,2-Dideoxy-3-phosphocholyl-5-n-hexadecyl-D-xylofuranose

Following the procedure of Example 9, α-methyl 2-deoxy-3-n-hexadecyl-D-xylofuranoside was reacted with $Et_3SiH$ and an equimolar amount of $BF_3$.etherate in acetonitrile/methylene dichloride solution. The reaction mixture was stirred for 90 minutes and then quenched with potassium carbonate. The product was isolated and purified by the procedure of Example 9 (chromatography over $SiO_2$, 5:1 cyclohexane/ethyl acetate). A 70% yield (0.13 g from 0.202 g of starting material) of 1,2-dideoxy-5-n-hexadecyl-D-xylofuranose having the following physical properties:

$R_f$=0.33 ($SiO_2$, Solvent A); MS (relative intensity): 343 (M+1, 100)

The above compound was converted to 1,2-dideoxy-3-phosphocholyl-5-n-hexadecyl-D-xylofuranose by the procedure of Example 10. This later compound had these physical characteristics:

$R_f$=0.28 ($SiO_2$, Solvent B); NMR ($CDCl_3$) δ 4.8 (m, 1, H-3) 4.3 (brd m, 2), 3.6–4.0 (brd m, b 5), 3.4 (brd s, 13), 2.2 (brd, m, 2)

Although all of the above examples deal with the preparation of compounds derived from 2-deoxy-D-ribose or 2-deoxy-D-xylose, it will be apparent that the same chemistry applied to the L forms of these 2-deoxy sugars, 2-deoxy-L-ribose and 2-deoxy-L-xylose will produce pharmaceutically active compounds having an "L" configuration.

The compounds of this invention inhibit PAF ($10^{-7}$ molar) induced human platelet aggregation at concentrations in the range 50–100 micromolar, but are aggregation inducers at higher concentrations. Human platelet aggregation experiments were performed using the method of Born (Nature, 194, 927 (1962)). Citrated platelet-rich plasma (2.5–4.0×$10^5$ platelets/ml) was used, and platelet aggregation was monitored at 37° C. with a Payton Aggregometer by the conventional optical density method. Platelets were treated with drug 2 minutes prior to addition of PAF, and optical density was measured 4 min later.

The compounds of this invention are also cytostatic in that they inhibit the growth of human leukemic cells (CCRF-CEM cell line). Table 1 below gives the results of the antileukemic testing of several compounds coming within the scope of formula II. In the Table, column 1 gives the structure of the compound, and column 2 the $IC_{50}$ (concentration giving 50% growth inhibition) in mcg/ml.

TABLE 1

Cell-Growth Inhibition of 2-Deoxy Five Carbon Sugars 3-phosphocholyl-5-n-straight-chain, aliphatic-D-ribose Series $$\begin{array}{c}\text{R} \quad \text{O} \quad \text{H} \\ \text{R}^1 \diagdown \diagup \text{////CH}_2\text{OC}_{16}\text{H}_{33} \\ \text{////H} \quad \text{O} \\ \text{O}-\text{P}-\text{O}-(\text{CH}_2)_2\text{N}^+(\text{CH}_3)_3 \\ \text{O}^- \end{array}$$

| R | $R^1$ | $IC_{50}$ mcg/ml |
|---|---|---|
| MeO | H | 2.3 |
| H | MeO | 6.2 |
| H(OH) | OH(H) | 6.4 |
| H | H | 3.7 |

3-n straight chain aliphatic-5-phosphocholyl D-ribose Series $$\begin{array}{c}\text{R} \quad \text{O} \quad \text{H} \quad \text{O} \\ \text{R}^1 \diagdown \diagup \text{////CH}_2\text{O}-\text{P}-\text{O}-(\text{CH}_2)_2\text{N}^+(\text{CH}_3)_3 \\ \text{////H} \quad \text{O}^- \\ \text{OC}_{16}\text{H}_{33} \end{array}$$

| R | $R^1$ | $IC_{50}$ mcg/ml |
|---|---|---|
| MeO | H | 5.2 |
| H | MeO | <2.1 |
| H(OH) | OH(H) | 13.2 |
| Carbonyl | | 6.2 |
| H | H | 3.4 |

3-phosphocholyl-5-n-straight chain aliphatic D-xylose Series

TABLE 1-continued

Cell-Growth Inhibition of 2-Deoxy
Five Carbon Sugars

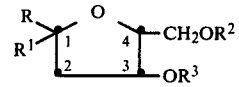

| R | R$^1$ | IC$_{50}$ mcg/ml |
|---|---|---|
| MeO | H | 5.3 |
| H | H | 6.2 |

Compounds according to formula II above are also active against transplanted tumors in mice. Table II which follows gives the results of testing α-methyl 2-deoxy-3-phosphocholyl-5-n-hexadecyl-D-ribofuranoside against X-5563, a plasma cell myeloma. In the table, column 1 gives the dosage levels, column 2 toxic deaths, column 3, the percent tumor growth inhibition and column 4, the dosage schedule or regimen. Ten mice were given each dosage ip and a group of 20 mice used as controls.

TABLE II

Antitumor Activity of α-Methyl
2-Deoxy-3-phosphocholyl-5-n-hexadecyl-D-ribofuranose

| dosage mg/kg | Toxic deaths | Percent inhibition of Tumor growth | Dosage/Regimen |
|---|---|---|---|
| 50 | 2/10 | 61 | Daily for 10 days |
| 25 | 0/10 | 37 | with 3 day delay. |

Certain of the compounds of this invention are also active in lowering the blood pressure of spontaneously hypertensive rats (SHR). For example, β-methyl 2-deoxy-3-phosphocholyl-5-n-hexadecyl-D-ribofuranoside, when administered subcutaneously to SHR at various dose levels, produced the hypotensive effects set forth in Table III below.

TABLE III

Hypertensive Activity of β-Methyl 2-Deoxy-
3-phosphocholyl-5-n-hexadecyl-D-ribofuranoside

| Dose mg/kg | No. of Rats | Time in Hours | Blood pressure* effect (mmHg) | Heart Rate |
|---|---|---|---|---|
| 5 | 8 | 3-5 | −20 | No effect |

*measured by tail-cuff method

The compounds of this invention are usually administered by the parenteral route; i.e., in emulplor (H$_2$O) in 5% acacia for ip administration, in saline for SC administration, or in 1.2% ethanol in saline for iv administration. For oral administration, the drug is added to 1% aqueous carboxymethyl cellulose, and the mixture placed in telescoping gelatin capsules, each capsule containing a unit dose.

We claim:

1. A tetrahydrofuran derivative of the formula

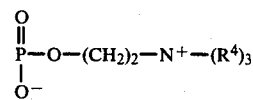

wherein, when taken singly, one of R and R$^1$ is C$_{1-3}$ alkoxy, or OH and the other is H; or both are H; and, when taken together with the carbon atom to which they are attached, form a carbonyl group; one of R$^2$ and R$^3$ is a C$_{10-18}$ straight chain aliphatic hydrocarbon and the other is a group of the formula $$\overset{O}{\underset{O^-}{\overset{\|}{P}}}-O-(CH_2)_2-N^+-(R^4)_3$$

wherein each R$^4$ is individually methyl or ethyl.

2. A compound according to claim 1 in which one of R$^2$ or R$^3$ is C$_{10-18}$ straight chain-alkyl.

3. A compound according to claim 2 in which one of R$^2$ or R$^3$ is n-hexadecyl.

4. A compound according to claim 1 in which R is β-methyl and R$^1$ is H.

5. A compound according to claim 1 in which R is a α-methyl and R$^1$ is H.

6. A compound according to claim 1 in which R and R$^1$ are both H.

7. A compound according to claim 1 in which the CH$_2$OR$^2$ group and the OR$^3$ group have a fixed trans orientation.

8. A compound according to claim 1 in which the C-3 hydroxyl and C-4 hydroxymethyl of the group tetrahydrofuran ring have the same orientation as in ribose.

9. A compound according to claim 1 in which all R$^4$'s (in the

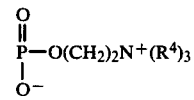

group) are CH$_3$.

10. A compound according to claim 3, said compound being β-methyl 2-deoxy-3-phosphocholyl-5-n-hexadecyl-D-ribofuranoside.

11. A compound according to claim 3, said compound being α-methyl 2-deoxy-3-phosphocholyl-5-n-hexadecyl-D-ribofuranoside.

12. A compound according to claim 3, said compound being β-methyl 2-deoxy-3-n-hexadecyl-5-phosphocholyl-D-ribofuranoside.

13. A compound according to claim 3, said compound being α-methyl 2-deoxy-3-n-hexadecyl-5-phosphocholyl-D-ribofuranoside.

14. A compound according to claim 1 in which the C-3 hydroxyl and C-4 hydroxymethyl group of the tetrahydrofuran ring have the same orientation as in xylose.

15. A compound according to claim 3, said compound being 1,2-dideoxy-3-phosphocholyl-5-n-hexadecyl-D-xylofuranose.

16. A compound according to claim 3, said compound being α-methyl 2-deoxy-3-n-hexadecyl-5-phosphocholyl-D-xylofuranoside.

* * * * *